United States Patent [19]

Micek

[11] Patent Number: 4,747,827

[45] Date of Patent: May 31, 1988

[54] NASOGASTRIC INTUBATION PROCESS

[76] Inventor: Frank C. Micek, 343 Ridge Rd., Barrington Hills, Ill. 60010

[21] Appl. No.: 911,429

[22] Filed: Sep. 25, 1986

[51] Int. Cl.⁴ ............................................ A61M 31/00

[52] U.S. Cl. ........................................ 604/54; 604/281

[58] Field of Search ...................... 128/207.18; 604/54, 604/280, 281, 282

[56] References Cited

U.S. PATENT DOCUMENTS

| | | | |
|---|---|---|---|
| 1,060,665 | 5/1913 | Bell | 604/281 |
| 2,393,003 | 1/1946 | Smith | 604/170 |
| 3,867,945 | 2/1975 | Long | 604/170 |
| 4,596,564 | 6/1986 | Spetzler et al. | 604/281 |

*Primary Examiner*—C. Fred Rosenbaum
*Assistant Examiner*—Gene B. Kartchner
*Attorney, Agent, or Firm*—Kinzer, Plyer, Dorn, McEachran & Jambor

[57] ABSTRACT

Nasogastric intubation process in which a stylet is employed to bend the tube to approximate the arch of the pharyngeal recess. After being so bent, the tube is inserted trans-pharyngeal recess until the tip is supra epiglottis. The stylet is withdrawn and the tube flexes adjacent the posterior esophageal wall for assured, quick passage to the stomach.

1 Claim, 1 Drawing Sheet

Fig. 1.
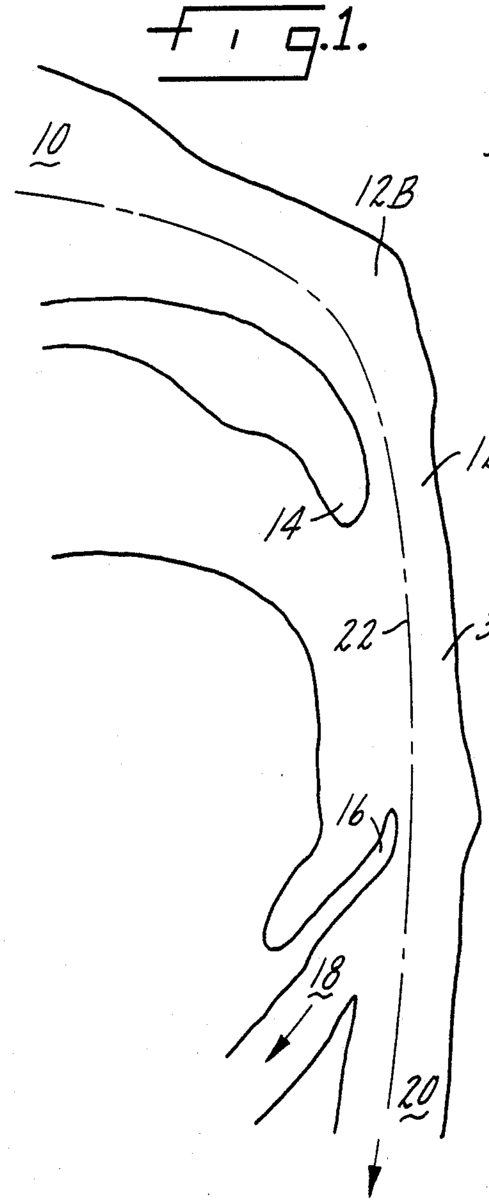
Fig. 3.
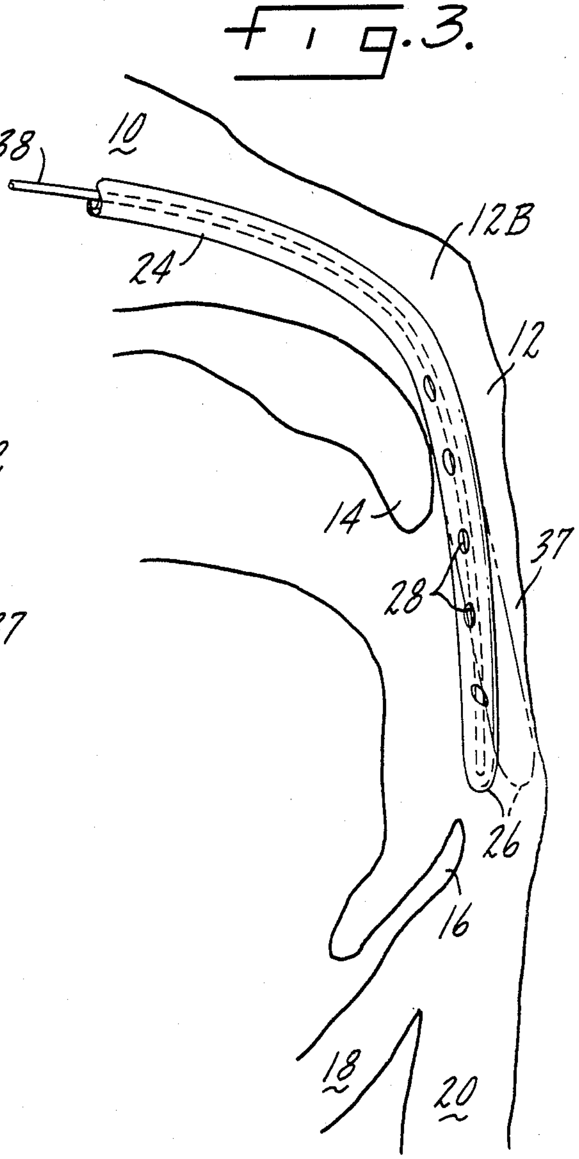
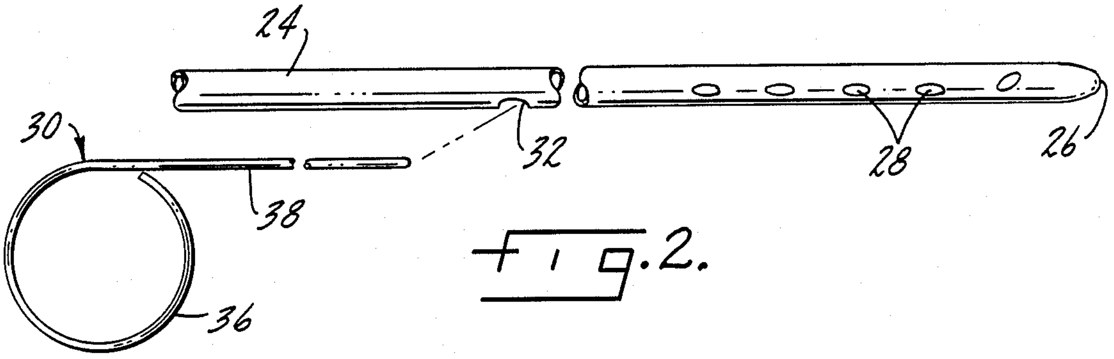
Fig. 2.

NASOGASTRIC INTUBATION PROCESS

BACKGROUND OF THE INVENTION

Nasogastric intubation is a medical process by which a flexible plastic tube (nasal-gastric tube) is passed through the nasal passage trans-soft palate, trans-pharyngeal recess, past (trans) the epiglottis and into the esophagus until the distal end section of the tube has been located in the stomach. The tube is perforated for a short distance at the distal end to permit negative pressure to be communicated to the stomach to withdraw fluids, or to permit fluids to be fed to the stomach through the tube, usually under emergency conditions. About six or seven inches of the tube will be located in the stomach. The present invention relates to an intubation technique.

The Problem

The nasal-gastric tube is relatively large in diameter (e.g. about 6 mm.) and somewhat thick walled because the negative pressure employed is sometimes intense. Therefore the tube must be strong enough to avoid collapse. The distal end is closed, not open, and consequently is somewhat rigid and tough.

The attendant, whether physician or skilled nurse, must be very careful during the insertion process not only to avoid delicate tissue trauma, but also to be certain the distal end of the tube does not enter the trachea, leading to the lungs, which is extremely undesirable for the well-being of the patient. The time required to assure passage of the tough end of the tube into the esophagus may be critical in emergency cases, where a few seconds may count, and the object of my invention is to assure that the nasal-gastric tube will be assuredly positioned for quick esophageal passage.

The nasal-gastric tube is a transparent plastic (e.g. polyvinyl) which, when flexed or bent, tends to return to its original unflexed state or position when the flexing bias is removed. I take advantage of this inherency to assure esophageal entry and at the same time I am able to facilitate trans-pharyngeal passage of the tube with limited chances of delicate tissue trauma. This is accomplished by inserting into the tube, prior to intubation, a stylet of soft malleable metal or other material easily bent into an arch so that when it is inserted in the tube the tube can be given a bend which approximates the physiological arch which extends from the area of the inferior concha across or past (trans) the pharyngeal recess to a position just above the epiglottis which guards the tracheo-esophageal orifices. Holding the tube with its end in this adjacent position, the stylet is then removed, whereupon the tube flexes in the direction of the posterior esophageal wall, that is, flexes away from the trachea so that the tube may be guided down the posterior esophageal wall with assurance of avoiding tracheal entry.

IN THE DRAWING

FIG. 1 is a schematic view of the interior of the human nasal-throat (pharynx) area, on an enlarged scale;

FIG. 2 is a detail view of a fragment of the distal end portion of a nasal-gastric tube combined with the stylet which features in the present invention;

FIG. 3 is a view similar to FIG. 1 but showing the intubation technique of the present invention.

DETAILED DESCRIPTION

FIG. 1 is a schematic view of the nasal-throat (pharynx) from the area of the inferior concha 10, transpharyngeal recess 12, trans-soft palate 14, trans-epiglottis 16 to the trachea (18) esophagus (20) branch. Physiologically, FIG. 1 is a schematic sagittal section showing the interior of the pharynx. The trans-section thus described (10 to 18-20) has an archlike profile identified by the dashed line 22. The external nares (end of the nose) is not shown.

In the course of nasogastric intubation, a nasal-gastric tube is so that the tube is forced along the arch 22 and is manipulated until the distal end has entered the esophageal passage 20 for final entry into the stomach.

It is, of course, of critical importance that the tube does not enter the trachea. The present invention addresses this problem.

In FIG. 2, a portion of the proximal end of a hollow nasal-gastric tube 24 is shown. The tube is transparent and has a soft exterior but it has relatively thick walls in order to assure against collapse when suction is employed. The tube has a solid distal end 26 and there are a series of perforations 28 in the tube extending distally, these perforations permitting communication of negative pressure to the stomach or the admission of fluids to the stomach depending upon the malady for which the patient is to be treated.

One object of the invention is to assure the tube enters the esophagus, not the trachea, and in achieving this object I utilize, FIG. 2, a stylet 30 of malleable metal such as copper, a soft bronze or a malleable iron-copper-tin alloy which can be inserted into the proximal portion of the tube and bent so that the tube will assume the general profile of the arch pharyngeal 22, FIG. 1.

Thus, as shown in FIG. 2, an opening 32 is made (or manufactured) in the tube rearward of the series of the perforations 28. This opening is located proximally of the closed end 26, a distance which allows ample room for the procedure now to be described.

The stylet will be provided at its proximal end with a handle or finger-grip 36. The stylet is held at the proximal end 36 and the free end is inserted through the slit 32, moving the stylet shaft down the tube passage (a length of 4" or 5") until the inserted end of the stylet has attained the solid or closed end 26 of the nasal-gastric tube.

Having positioned the stylet in the nasal-gastric tube, the attendant, thoroughly skilled in physiology and the insertion technique, bends the stylet until a profile is achieved which approximates the form of arch 22. The tube can be held up next to the patient's face to make the physiologic bend and estimate the approximate distance from the external nares to the posterior oral pharynx. The malleable stylet allows rebending in the cut-and-try sense. The tube thus bent is advanced into the nasal passage and is gently guided trans-pharyngeal recess and trans-soft palate until the distal end 26, FIG. 3, is supra adjacent the epiglottis 16, that is, located in the posterior pharynx 37 just above the epiglottis. Holding the tube in this adjacent position, the stylet is withdrawn, whereupon the last two inches or so of the tube flexes and tends to straighten itself into its original position, the distal end 26 thus moving against the posterior wall of the esophagus tract as shown by dashed line in FIG. 3, that is, away from the trachea 18. The tube is thus positioned for clear and direct movement down the esophagus and eventual location in the stomach as intended; the insertion opening 32 will be located in the stomach along with the communicating apertures 28.

The distance along the arch from the external nares to the posterior pharynx is nearly the same for all human adults, about thirteen centimeters (5″). This is the distance (maybe a few mms. less) that the insertion opening 32 will be spaced from the end 26 of the tube. This is also the minimum length of the stylet shaft 38 and thus the handle 36 will be positioned at the external nares when the tube is properly inserted as shown in FIG. 3. The shaft may be longer since the distance the handle 36 is conveniently displaced from the external nares is not important.

In pushing the loose tube into and through the anatomical recesses thus described, without the stylet, it is sometimes difficult to get through the approximate 90° bend 12B leading into the pharyngeal recess without some trauma caused by the tough, blunt end 26 of the tube; also, the nasal mucosa is friable and highly vascular, easily damaged. Moreover, in doing this, the distal end of the (unsupported) tube tends to point itself toward the trachea as it advances along the curved axis 22. The stylet, in comparison, reduces the chance of trauma because it aids and expedites "threading" the approximate 90° bend and, as already noted, the tube end portion, upon removal of the stylet, flexes posteriorly away from the trachea in comparison to the tendency to point itself toward the trachea when the tube is unsupported.

It may also be mentioned these tubes, as presently supplied, are sometimes referred to as N-G tubes, about thirty inches long and anywhere from "10 to 20 French," meaning 4–10 mm. in diameter. The stylet, as noted, may be any malleable material which will hold its shape when bent, like a wire coat hanger.

I claim:

1. Method of performing nasal-gastric intubation incidental to extending to the stomach a hollow flexible, nasal-gastric tube employed for intubation, the tube having a closed distal end and a series of perforations distally thereof to communicate negative pressure to the stomach or to pass fluids to the stomach, and the tube when flexed tending to return to its original unflexed attitude, said method comprising:

inserting into the perforated portion of the tube a stylet having a shaft of malleable material, which holds its shape when bent, until the inserted end of the stylet reaches the distal end of said tube, and then bending the stylet to cause the tube to assume an arch profile which approximates the arch-like passage from the inferior concha past (trans) the pharyngeal recess and well into the posterior pharynx;

inserting the arched tube containing the bent stylet trans-pharyngeal recess and trans-soft palate until the distal end of the tube is positioned adjacent the epiglottis;

holding the tube in said adjacent position and withdrawing the stylet to allow the distal end of the tube to flex toward the posterior wall of the esophagus away from the trachea thereby biasing the tube for sure entry into the esophagus; and advancing the tube down the esophagus into the stomach.

* * * * *